United States Patent

Schmidt et al.

(10) Patent No.: US 12,322,090 B2
(45) Date of Patent: Jun. 3, 2025

(54) MACHINE LEARNING-ASSISTED COMPUTED TOMOGRAPHY WORKFLOW

(71) Applicant: Siemens Healthineers AG, Forchheim (DE)

(72) Inventors: Bernhard Schmidt, Fürth (DE); Katharine Grant, Rochester, MN (US)

(73) Assignee: Siemens Healthineers AG, Forchheim (DE)

( * ) Notice: Subject to any disclaimer, the term of this patent is extended or adjusted under 35 U.S.C. 154(b) by 391 days.

(21) Appl. No.: 17/664,126

(22) Filed: May 19, 2022

(65) Prior Publication Data

US 2023/0410289 A1    Dec. 21, 2023

(51) Int. Cl.
| | |
|---|---|
| *G06T 7/00* | (2017.01) |
| *G06T 7/73* | (2017.01) |
| *G06V 10/25* | (2022.01) |
| *G06V 10/77* | (2022.01) |
| *G16H 30/20* | (2018.01) |

(52) U.S. Cl.
CPC .............. *G06T 7/0012* (2013.01); *G06T 7/73* (2017.01); *G06V 10/25* (2022.01); *G06V 10/7715* (2022.01); *G16H 30/20* (2018.01); *G06T 2207/30044* (2013.01)

(58) Field of Classification Search
CPC ............. G06T 7/0012; G06T 7/73; G06T 2207/30044; G06V 10/25; G06V 10/7715; G06V 10/764; G06V 10/774; G16H 30/20; A61B 6/488; A61B 6/5217; A61B 6/545; A61B 6/032
See application file for complete search history.

(56) References Cited

U.S. PATENT DOCUMENTS

| | | | |
|---|---|---|---|
| 10,463,317 B2* | 11/2019 | Tian | A61B 6/032 |
| 2010/0034356 A1* | 2/2010 | Hayashida | H04L 67/12 |
| | | | 378/98 |
| 2010/0163758 A1* | 7/2010 | Kirschenbaum | G21F 3/02 |
| | | | 250/516.1 |
| 2014/0119630 A1* | 5/2014 | Sowards-Emmerd | |
| | | | G16H 50/30 |
| | | | 382/131 |

(Continued)

FOREIGN PATENT DOCUMENTS

WO    2021062173 A1    4/2021

OTHER PUBLICATIONS

Gomes, Juliana, Grace J. Gang, Aswin Mathews, and J. Webster Stayman. "An investigation of low-dose 3D scout scans for computed tomography." In Medical Imaging 2017: Physics of Medical Imaging, vol. 10132, pp. 677-682. SPIE, 2017. (Year: 2017).*

(Continued)

*Primary Examiner* — Wassim Mahrouka

(57) ABSTRACT

A system and method include acquisition of a two-dimensional radiograph of a patient, input of the radiograph to a trained machine learning model to generate a classification, performance of a computed tomography scan of the patient based on the two-dimensional radiograph if the classification indicates that the patient does not have a first condition, and determination to modify the computed tomography scan if the classification indicates that the patient has the first condition.

9 Claims, 5 Drawing Sheets

(56) References Cited

U.S. PATENT DOCUMENTS

| | | | |
|---|---|---|---|
| 2015/0100290 A1* | 4/2015 | Falt | G16H 50/50 |
| | | | 703/2 |
| 2016/0154931 A1* | 6/2016 | Zheng | G16B 30/00 |
| | | | 702/19 |
| 2016/0300041 A1* | 10/2016 | Adriaensens | G16H 20/30 |
| 2019/0133544 A1* | 5/2019 | Liu | G06T 7/73 |
| 2020/0094074 A1 | 3/2020 | Chen et al. | |
| 2021/0282730 A1 | 9/2021 | Singh et al. | |
| 2022/0338819 A1* | 10/2022 | Stayman | A61B 6/545 |

OTHER PUBLICATIONS

Diniz ("Deep learning strategies for ultrasound in pregnancy." European Medical Journal. Reproductive health 6, No. 1 (2020): 73.). (Year: 2020).*
ESR dated Oct. 17, 2023 in EP application No. 23173718.0, 7 pages.

* cited by examiner

MACHINE LEARNING-ASSISTED COMPUTED TOMOGRAPHY WORKFLOW

BACKGROUND

Conventional medical imaging systems are capable of generating high-quality images of internal structures and processes. Medical imaging is therefore commonly used for disease prevention and diagnosis. Many types of medical imaging exist, including x-ray imaging, computed tomography (CT) imaging, positron emission tomography (PET) imaging, single photon emission computed tomography (SPECT), and magnetic resonance (MR) imaging.

According to CT imaging, a narrow beam of x-rays is emitted towards a patient and detected on an opposite side of the patient while the emitter and detector are rotated around the patient. The detected signals are processed to generate cross-sectional images (i.e., "slices") of the patient. Successive slices may be combined to form a three-dimensional image that facilitates identification of internal structures and any tumors or other abnormalities.

CT images typically contain more information than conventional two-dimensional x-ray images. However, the acquisition of a CT image subjects a patient to significantly more radiation exposure than the acquisition of a conventional x-ray image. Consequently, a patient may have a condition which requires limiting or avoiding significant radiation exposure to a portion (or all) of the body, but the condition cannot be detected or is otherwise unknown prior to acquisition of a CT image.

In one example, and although standard practice is to avoid acquiring a CT image of a pregnant female, pregnancy might be unknown until it is detected in a CT image. At this point it is too late to avoid radiation exposure to the fetus. Current systems may attempt to estimate the radiation exposure in retrospect and take any suitable remedial actions.

Systems are desired to efficiently detect a patient condition and change CT imaging parameters based on the detected condition within a CT imaging workflow.

DETAILED DESCRIPTION

The following description is provided to enable any person in the art to make and use the described embodiments and sets forth the best mode contemplated for carrying out the described embodiments. Various modifications, however, will remain apparent to those in the art.

Some embodiments use a trained classification model to detect a patient condition based on a radiograph acquired by a CT scanner prior to a CT scan. The radiograph may comprise a low-resolution two-dimensional image of a patient lying on a scanning bed and is typically used to determine the scanning range of a subsequent CT scan based on locations of bony structures and lungs, and/or to derive attenuation information for automatic exposure control. If the patient condition (e.g., pregnancy) is detected, the subsequent imaging process can be adapted accordingly (e.g., adjust scan area, select different imaging modality). Embodiments may therefore efficiently avoid undesirable radiation exposure in view of a patient condition that might not have been visually detectable within the radiograph. Advantageously, some embodiments train the classification model using a set of radiographs which are labeled (e.g., pregnant, not pregnant) by evaluating associated CT images for the given patient condition, as will be described below.

Figure 1:
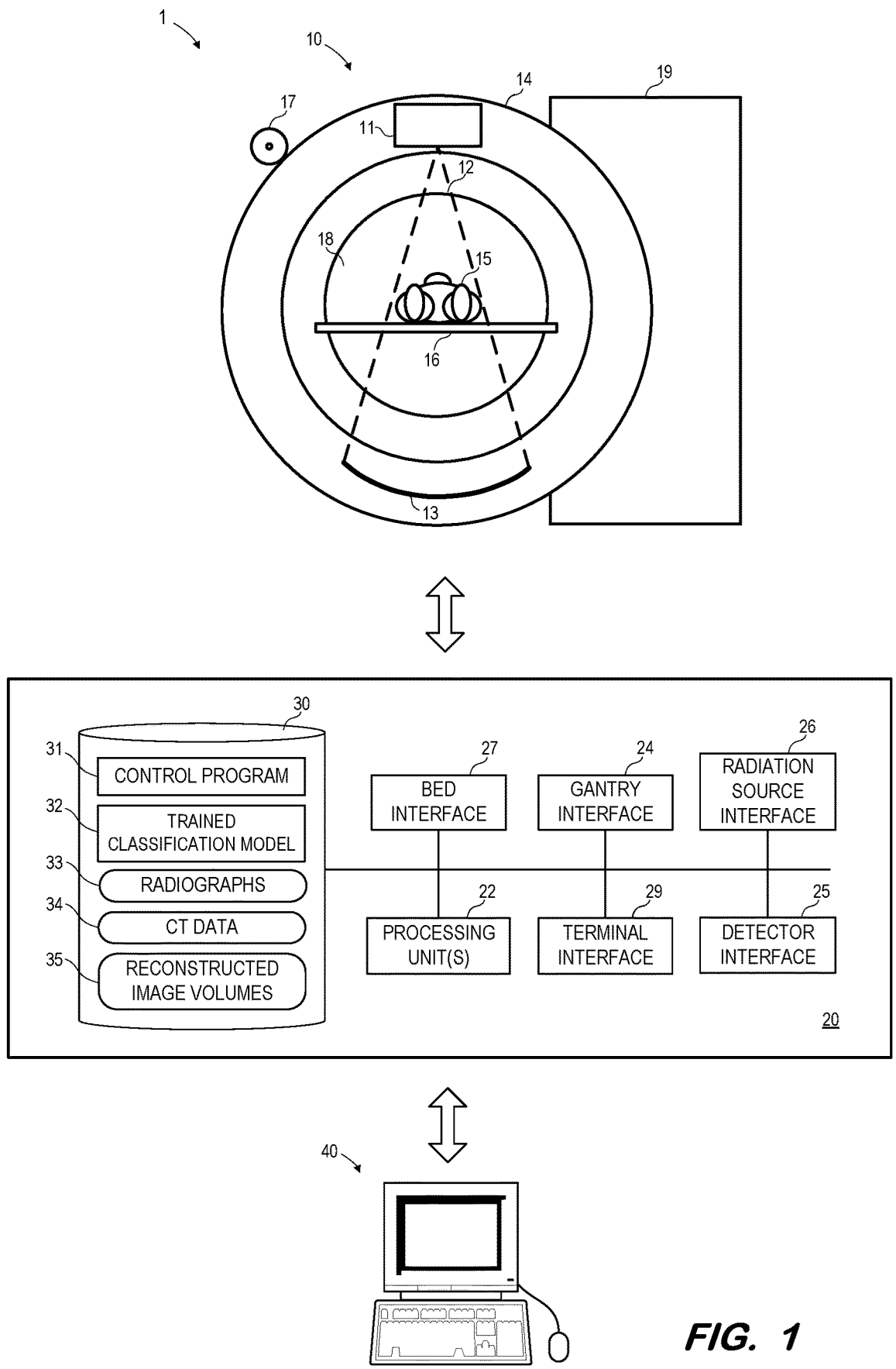
FIG. 1 is a block diagram of a CT imaging system including a trained classification model according to some embodiments.

FIG. 1 is a block diagram of CT imaging system 1 according to some embodiments. Imaging system 1 comprises CT scanner 10 including x-ray source 11 for emitting x-ray beam 12 toward opposing radiation detector 13. X-ray source 11 and radiation detector 13 are mounted on gantry 14 such that they may be rotated about a center of rotation of gantry 14 while maintaining the same physical relationship therebetween.

Patient 15 is positioned on bed 16 to place a portion of patient 15 between x-ray source 11 and radiation detector 13. Next, x-ray source 11 and radiation detector 13 are moved to various projection angles with respect to patient 15 by using rotation drive 17 to rotate gantry 14 around cavity 18 in which patient 15 is positioned. At each projection angle, x-ray source 11 is powered by high-voltage generator 19 to transmit x-ray radiation 12 toward detector 13. Detector 13 receives the radiation and produces a set of data (i.e., a raw image) for each projection angle, representing the attenuative properties of patient 15 from the perspective of the projection angle.

The width of beam 12 in the z-direction (along the length of the patient and cavity 18) spans a few inches and therefore the set of data (i.e., a raw image) for each projection angle represents a slice of patient 15 taken perpendicular to the z-direction. By moving bed 16 in the z-direction, data representing other slices of patient 15 may be similarly acquired.

Radiation detector 13 may comprise any system to acquire an image based on received x-ray radiation. In some embodiments, radiation detector 13 uses a scintillator layer and solid-state amorphous silicon photodiodes deployed in a two-dimensional array. The scintillator layer receives photons and generates light in proportion to the intensity of the received photons. The array of photodiodes receives the light and records the intensity of received light as stored electrical charge.

In other embodiments, radiation detector 13 converts received photons to electrical charge without requiring a scintillator layer. The photons are absorbed directly by an array of amorphous selenium photoconductors. The photoconductors convert the photons directly to stored electrical charge.

System 20 may comprise any general-purpose or dedicated computing system. Accordingly, system 20 includes one or more processing units 22 configured to execute program code to cause system 20 to operate as described herein, and storage device 30 for storing the program code. A processing unit may comprise a processor, a processor core, or a processor thread. Storage device 30 may comprise one or more fixed disks, solid-state random access memory, and/or removable media (e.g., a thumb drive) mounted in a corresponding interface (e.g., a USB port).

Storage device 30 stores program code of control program 31. One or more processing units 22 may execute control program 31 to determine imaging parameters, to rotate gantry 14, to move bed 16, to cause radiation source 11 to emit radiation at desired energies, and to control detector 13 to acquire CT data 34. In this regard, system 20 includes gantry interface 24, detector interface 25, radiation source interface 26 and bed interface 27 for communication with corresponding elements of scanner 10. System 20 may also receive input from terminal 40 which may be used to control image acquisition.

CT data 34 may be stored in DICOM or another data format. CT data 34 may be further associated with of acquisition details, including but not limited to imaging plane position and angle, imaging position, radiation source-to-detector distance, patient anatomy imaged, patient position, contrast medium bolus injection profile, x-ray tube voltage, image resolution and radiation dosage. Processing units 22 may execute control program 31 to reconstruct three-dimensional images volumes 35 from CT data 34 as is known in the art.

System 20 may operate scanner 10 to acquire radiographs 33 as is known in the art. A radiograph is a two-dimensional image representing a single perspective. To acquire a radiograph according to one example, source 11 is maintained at a fixed position with respect to gantry 14 and emits beam 12 toward detector 13. Contemporaneously, bed 16 is moved to pass patient 15 lengthwise through the beam 12.

A radiograph is typically acquired in the above manner prior to a CT scan to determine/confirm a location of patient anatomy with respect to CT scanner 10. Acquisition of a radiograph delivers a much smaller radiation dose to the patient than that delivered during a CT scan.

Trained classification model 32 comprises executable program code implementing a trained machine learning algorithm. As will be described in detail below, a radiograph 33 is input to model 32 and model 32 outputs a patient condition in response. Based on the condition, a subsequent CT scan may be modified, aborted or executed. In one example, a radiograph of a patient is acquired in preparation for a subsequent CT scan. The radiograph is input to model 32, and model 32 indicates that the patient is pregnant. In response to this indication, the planned CT scan is not performed.

CT data 34 and/or image volumes 35 may be provided to terminal 40 for display. Terminal 40 may comprise a display device and an input device coupled to system 20. In some embodiments, terminal 40 is a separate computing device such as, but not limited to, a desktop computer, a laptop computer, a tablet computer, and a smartphone. Terminal 40 displays images received from system 20, receives user input for controlling scanner 10 and system 20, and transmits such user input to system 20.

Each of scanner 10, system 20 and terminal 40 may include other elements which are necessary for the operation thereof, as well as additional elements for providing functions other than those described herein.

Embodiments are not limited to a CT scanner as described above with respect to FIG. 1. For example, embodiments may employ a dual-arm CT scanner using two radiation sources and corresponding detectors. Such systems may acquire CT data from two different projection angles substantially simultaneously.

Figure 2:
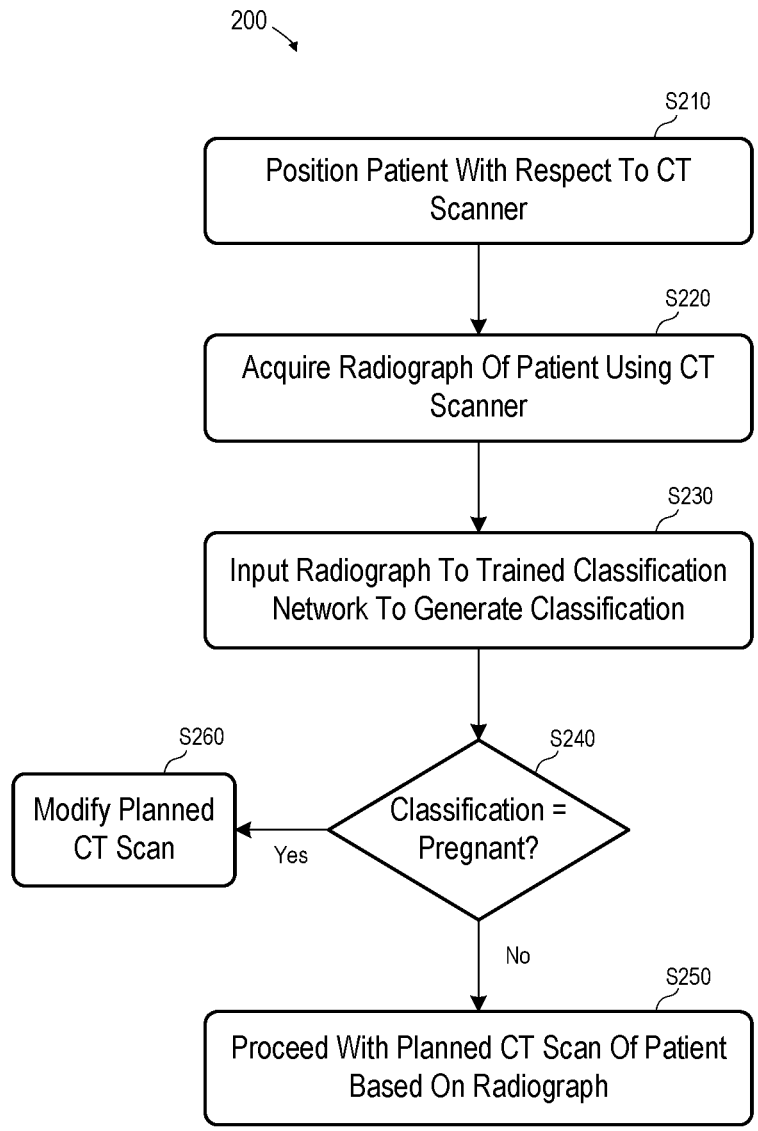
FIG. 2 is a flow diagram of a CT imaging workflow according to some embodiments.

FIG. 2 comprises a flow diagram of process 200 according to some embodiments. Process 200 and the other processes described herein may be performed using any suitable combination of hardware, software or other means. Software embodying these processes may be stored by any non-transitory tangible medium, including but not limited to a fixed disk, a DVD, a Flash drive, or a magnetic tape. Examples of these processes will be described below with respect to the elements of system 1, but embodiments are not limited thereto.

Initially, at S210, a patient is positioned with respect to a CT scanner. The patient is typically positioned according to a predetermined imaging plan. Such positioning may include alignment of the patient with markers placed or projected on the CT scanner and/or the patient as is known in the art. Positioning of the patient may include positioning of any suitable imaging accessories, including but not limited to radiation-shielding devices, stabilization devices, etc.

A radiograph of the patient is acquired using the CT scanner at S220. As described above, the radiograph may be acquired by moving the patient past a stationary and operating radiation source and detector. The radiograph may be performed as part of the typical scanning workflow. The radiograph may be used to verify a position of the patient as is known in the art.

According to some embodiments, the radiograph is also input to a trained classification network at S230 to generate a classification. In the present example, the classification network has been trained to classify the input radiograph as pregnant or not pregnant. Embodiments are not limited to this condition. In some embodiments, the trained classification network inputs a probability for one or both of the potential classifications (e.g., 72% pregnant; 15% not pregnant).

At S240, it is determined whether the output classification indicates that the patient is pregnant. This determination may include evaluation of the one or more probabilities output by the classification model against various thresholds. For example, the patient may be considered pregnant at S240 only if the output probability associated with the classification pregnant is greater than 70%.

If the determination at S240 is negative, the originally-planned CT scan is executed at S250. If the determination at S240 is negative, the planned CT scan is modified at S260. The modification may consist of aborting the CT scan entirely, of shielding the fetus, of reducing radiation delivered to the reproductive organs, and/or any combination of modifications. Advantageously, such modification allows avoidance of undesirable radiation exposure in view of a patient condition that might not have been visually detectable within the acquired radiograph.

Figure 3:
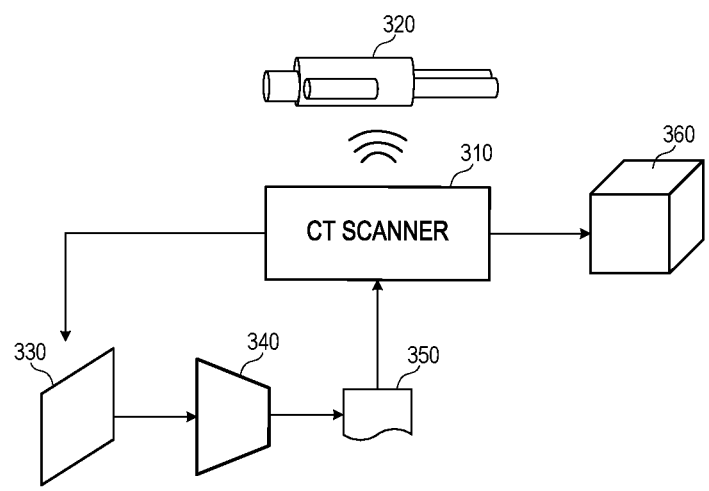
FIG. 3 is a block diagram illustrating use of a trained classification model during a CT imaging workflow according to some embodiments.

FIG. 3 is a block diagram illustrating a process according to some embodiments. Patient 320 is positioned in an imaging position with respect to CT scanner 310 in preparation for a CT scan. CT scanner 310 operates its x-ray source and detector to acquire radiograph 330. Radiograph 330 is then input to trained classification network 340 to generate classification 350. Based on classification 350, it is determined whether to continue with the CT scan, modify the CT scan and execute the modified CT scan, or abort the CT scan. If it is determined to execute the CT scan, the CT scan may result in reconstructed volume 360 as is known in the art.

Figure 4:
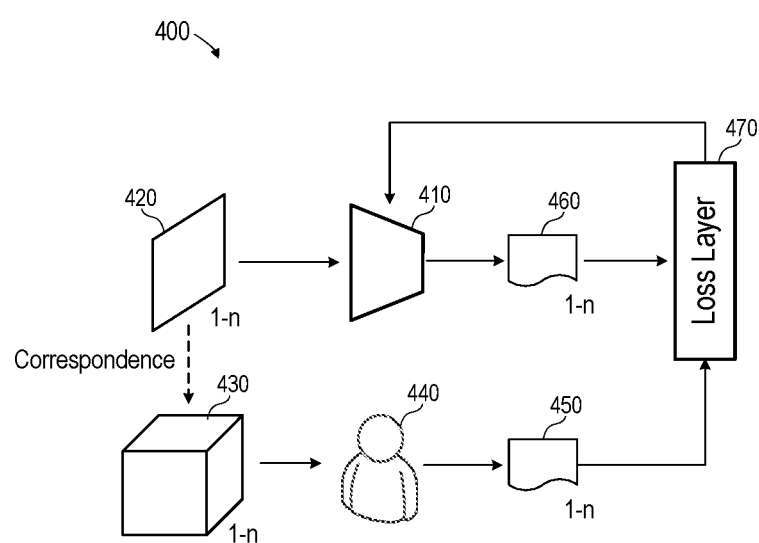
FIG. 4 is a block diagram illustrating training of a classification model to detect a condition based on a radiograph according to some embodiments.

FIG. 4 illustrates training of a classification model according to some embodiments. Generally, architecture 400 trains model 410 to implement a function. The training is based on training radiographs$_{1-n}$ 420 and corresponding ground truth labels$_{1-n}$ 450 determined based on associated CT volumes$_{1-n}$ 430.

Model 410 may comprise any type of learning network that is or becomes known. Broadly, model 410 may comprise a network of neurons which receive input, change internal state according to that input, and produce output depending on the input and internal state. The output of certain neurons is connected to the input of other neurons to form a directed and weighted graph. The weights as well as the functions that compute the internal state can be modified via training as will be described below. Model 410 may comprise any one or more types of artificial neural network that are or become known, including but not limited to convolutional neural networks, recurrent neural networks, long short-term memory networks, deep reservoir computing and deep echo state networks, deep belief networks, and deep stacking networks.

Radiographs$_{1-n}$ 420 and CT volumes$_{1-n}$ 430 may be acquired from any one or more image volume repositories. Each radiograph$_x$ corresponds to a CT volume$_x$. Although embodiments are not limited thereto, it is assumed that radiograph$_x$ and its corresponding CT volume$_x$ are acquired by a same CT scanner of a same patient relatively contemporaneously. In other words, a radiograph$_x$ of a given patient may have been acquired by a given CT scanner prior to acquisition of CT volume$_x$ of the given patient by the given CT scanner. In order to increase robustness of the learned function, radiographs$_{1-n}$ 420 may be acquired by many different CT scanners of many different patients using many different CT scanning settings.

Observer 440 determines ground truth labels$_{1-n}$ 450 based on CT volumes$_{1-n}$ 430. Observer 440 reviews each of CT volumes$_{1-n}$ 430 for the existence of a given condition and generates a corresponding label 450 indicating whether the CT volume exhibits the condition. As noted above, certain conditions may be easier to identify in a CT volume 430 than in its corresponding radiograph 420. Observer 440 may comprise one or more humans and/or automated systems, such as a trained machine learning model.

During training, a batch of radiographs$_{1-n}$ 420 is input to model 410. Model 410 operates according to its initial configuration to output a corresponding batch of inferred labels$_{1-n}$ 460. Loss layer 470 determines a loss by comparing the batch of inferred labels$_{1-n}$ 460 with corresponding ones of ground truth labels$_{1-n}$ 450. Generally, the determined loss reflects a difference between the batch of inferred labels$_{1-n}$ 460 and corresponding ones of ground truth labels$_{1-n}$ 450.

As is known in the art, the loss is back-propagated to model 410 in order to modify model 410 in an attempt to minimize the loss. The process repeats and model 410 is iteratively modified in this manner until the loss reaches acceptable levels or training otherwise terminates (e.g., due to time constraints or to the loss asymptotically approaching a lower bound). At this point, model 410 is considered trained. Trained model 410 may be subjected to testing. If the performance of trained model is not sufficient, model 410 may be re-trained using different training parameters.

According to some embodiments, observer 440 may review CT volumes$_{1-n}$ 430 for the existence of several conditions. Each of ground truth labels$_{1-n}$ 450 may then provide indications of whether each of the several conditions is present in its corresponding CT volume. Model 410 may be configured and trained to output probabilities for each of the several conditions. During deployment of such a trained model 410, the model is used to detect the presence of conditions based on an acquired radiograph as described with respect to process 200, and a planned CT scan may be modified based on the presence of one or more conditions.

Figure 5:
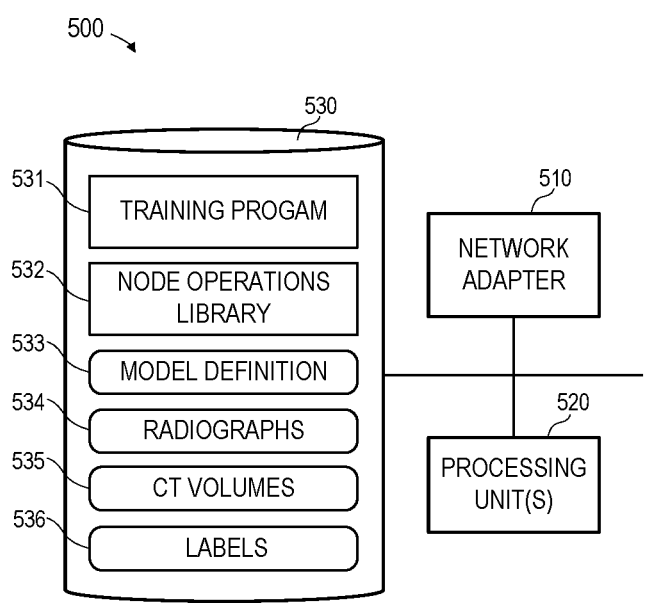
FIG. 5 is a block diagram of an apparatus to train a classification model according to some embodiments.

FIG. 5 illustrates computing system 500 according to some embodiments. System 500 may comprise a computing system to facilitate the design and training of a machine learning model as is known in the art. Computing system 500 may comprise a standalone system, or one or more elements of computing system 500 may be located in the cloud.

System 500 includes network adapter 510 to communicate with external devices via a network connection. Processing unit(s) 520 may comprise one or more processors, processor cores, or other processing units to execute processor-executable program code. In this regard, storage system 530, which may comprise one or more memory devices (e.g., a hard disk drive, a solid-state drive), stores processor-executable program code of training program 531 which may be executed by processing unit(s) 520 to train a model as described herein.

Training program 531 may utilize node operations library 532, which includes program code to execute various operations associated with node operations as defined in node operations library 532. According to some embodiments, computing system 500 provides interfaces and development software (not shown) to enable development of training program 531 and generation of model definition 534. Storage device 530 also includes training data consisting of radiographs 534, CT volumes 535 and labels 536.

Those in the art will appreciate that various adaptations and modifications of the above-described embodiments can be configured without departing from the claims. Therefore, it is to be understood that the claims may be practiced other than as specifically described herein.

What is claimed is:

1. A system comprising:
an imaging system; and
a computing system to:
plan a computed tomography scan of a patient;
operate the imaging system to acquire a two-dimensional radiograph of the patient;
input the radiograph to a trained machine learning model;
receive from the trained machine learning model, in response to the input radiograph, a classification indicating whether the patient is pregnant or not pregnant;
if the classification indicates that the patient is not pregnant, operate the imaging system to perform the computed tomography scan of the patient based on the two-dimensional radiograph; and
if the classification indicates that the patient is pregnant, shield a fetus within the patient, modify the computed tomography scan to reduce radiation delivered to reproductive organs of the patient, and operate the imaging system to perform the modified computed tomography scan.

2. A system according to claim 1, wherein the model is trained based on a plurality of radiographs and a classification corresponding to each radiograph, wherein the classification corresponding to a radiograph is determined based on a computed tomography volume generated contemporaneously to the radiograph.

3. A system according to claim 1,
wherein the model is trained based on a plurality of radiographs and a plurality of classifications corresponding to each radiograph, wherein the plurality of classifications corresponding to a radiograph are determined based on a computed tomography volume generated contemporaneously to the radiograph.

4. A method comprising:
planning a computed tomography scan of a patient;
acquiring a two-dimensional radiograph of the patient;

inputting the radiograph to a trained machine learning model;

receiving from the trained machine learning model, in response to the input radiograph, a classification indicating whether the patient is pregnant or not pregnant;

if the classification indicates that the patient is not pregnant, performing the computed tomography scan of the patient based on the two-dimensional radiograph; and if the classification indicates that the patient is pregnant, shielding a fetus within the patient, modifying the computed tomography scan to reduce radiation delivered to reproductive organs of the patient, and operating an imaging system to perform the modified computed tomography scan.

5. A method according to claim 4, wherein the model is trained based on a plurality of radiographs and a classification corresponding to each radiograph, wherein the classification corresponding to a radiograph is determined based on a computed tomography volume generated contemporaneously to the radiograph.

6. A method according to claim 4, wherein the model is trained based on a plurality of radiographs and a plurality of classifications corresponding to each radiograph, wherein the plurality of classifications corresponding to a radiograph are determined based on a computed tomography volume generated contemporaneously to the radiograph.

7. A system comprising:

a storage device storing a trained classification model; and a processing unit to:

plan a computed tomography scan of a patient;

input a two-dimensional radiograph of the patient to the trained classification model;

receive from the trained machine learning model, in response to the input radiograph, a classification indicating whether the patient is pregnant or not pregnant;

if the classification indicates that the patient is not pregnant, operate an imaging system to perform the computed tomography scan of the patient based on the two-dimensional radiograph; and if the classification indicates that the patient is pregnant, shield a fetus within the patient, modify the computed tomography scan to reduce radiation delivered to reproductive organs of the patient, and operate the imaging system to perform the modified computed tomography scan.

8. A system according to claim 7, wherein the model is trained based on a plurality of radiographs and a classification corresponding to each radiograph, wherein the classification corresponding to a radiograph is determined based on a computed tomography volume generated contemporaneously to the radiograph.

9. A system according to claim 7, wherein the model is trained based on a plurality of radiographs and a plurality of classifications corresponding to each radiograph, wherein the plurality of classifications corresponding to a radiograph are determined based on a computed tomography volume generated contemporaneously to the radiograph.

* * * * *